United States Patent [19]

Elkins

[11] Patent Number: 4,869,259

[45] Date of Patent: Sep. 26, 1989

[54] ECHOGENICALLY ENHANCED SURGICAL INSTRUMENT AND METHOD FOR PRODUCTION THEREOF

[75] Inventor: Dexter J. Elkins, Bloomington, Ind.

[73] Assignees: Vance Products Incorporated; Cook Urological Incorporated, both of Spencer, Ind.

[21] Appl. No.: 194,861

[22] Filed: May 17, 1988

[51] Int. Cl.⁴ .............................................. A61B 8/00
[52] U.S. Cl. ............................... 128/660; 128/667.05; 604/272
[58] Field of Search ...................... 128/662.02, 662.05; 604/100, 264, 272–274

[56] References Cited

U.S. PATENT DOCUMENTS 2,711,733  6/1955  Jacoby, Jr. ........................... 604/274
4,207,901  6/1980  Nigam .
4,249,539  2/1981  Vilkomerson et al. .
4,401,124  9/1983  Guess et al. .
4,402,324  9/1983  Lindgren et al. .
4,431,006  2/1984  Trimmer et al. .
4,490,139  12/1984  Huizenga et al. ............... 604/272 X
4,567,896  2/1986  Barnes et al. .

Primary Examiner—Francis Jaworski
Attorney, Agent, or Firm—Woodard, Emhardt, Naughton, Moriarty & McNett

[57] ABSTRACT

A surgical instrument such as a needle is particle-blasted with particles approximately 50 microns in diameter to produce a uniformly roughened surface portion for use with an ultrasound imaging system to provide real-time monitoring of the location of a specific portion of the needle during insertion and guidance inside the patient's body.

21 Claims, 1 Drawing Sheet

ECHOGENICALLY ENHANCED SURGICAL INSTRUMENT AND METHOD FOR PRODUCTION THEREOF

FIELD OF THE INVENTION

The present invention relates to devices for use in an ultrasonic imaging systems and more particularly to an echogenically enhanced surgical instrument.

BACKGROUND OF THE INVENTION

During the past several decades, ultrasonic imaging techniques have become increasingly prevalent in clinical diagnoses, and more particularly in obstetrics, gynecology and urology. Specialists in these disciplines use ultrasound to image a wide variety of medical abnormalities including malignant and non-malignant cysts and tumors and fetal status in utero as well as "real-time" monitoring of needle location during such procedures as fetal blood sampling, amniocentesis, tissue aspiration biopsy and core biopsy. Considerable effort has been expended to significantly enhance the ultrasound image of a needle, or at least its point or tip, in order to more accurately pinpoint its placement or advancement over real-time ultrasonic guidance. Not only is accurate guidance required to obtain the proper sample, but it is also necessary to avoid puncturing or damage to tissues.

The term echogenicity refers to the relative, intrinsic or innate degree or extent that a surface reflects incident ultrasound wave energy directly back to sensor, which is proximal to the source or emitter. The degree of echogenicity is directly interdependent on two primary factors, according to essential ultrasound physics: (1) the density of the "target" receiving and reflecting the sound energy, and (2) the elasticity of the "target" being ultrasonically imaged. These two factors are professed to be the essential reasons why air and/or water in tissue or organs are more "echogenic" or alter the echogenicity. The same applies to (dense) metal, such as the shaft of a needle.

Guess et al. U.S. Pat. No. 4,401,124 outlines some of the problems associated with monitoring the insertion and guidance of needles and other instruments. The Guess et al. patent also discloses a proposed solution to the monitoring problem by providing, in an ultrasound pulse-echo imaging system, a defraction granting disposed on the surface of the surgical instrument. The defraction grating is disclosed to have a specified distance D between the depth of adjacent grooves, that distance D being a function of various parameters including the center wavelength λ of the transducer and the angle θ between the incident beam and a line along the surface of the instrument and perpendicular to the grooves. The Guess et al. reference also discloses other attempts directed toward monitoring the location of a surgical instrument, such as a needle, inside the body as well as discussing their drawbacks.

Although the Guess et al. system with its helical defraction grating around the tip of the needle, along with other needles having similar rings, may provide some degree of signal reinforcement along the axis of incident energy, the overall image is far from ideal. Further, needles of this type typically exhibit a marked loss of resolution as the needle is oriented away from an optimum angle relative to the incident ultrasound beam, which angle depends upon the particular ring parameters.

What is needed is a device which provides more accurate monitoring of a surgical instrument such as a needle inserted into the body, which does not require a specific angle of orientation for its efficiency, and which is inexpensive to manufacture.

SUMMARY OF THE INVENTION

A surgical instrument is provided which has been treated to significantly enhance the ultrasound image of a portion of the instrument. A needle which is to be inserted and guided through the body for fetal blood sampling, amniocentesis or tissue aspiration biopsy, for example, is used with an ultrasound imaging system to provide real-time monitoring of the needle location. A specific portion of the exterior surface of the needle is uniformly and randomly particle-blasted with particles approximately 50 microns in diameter. Various particulate materials such as sand (silicon dioxide), silicon carbide and metal silicates can be used.

It is an object of the present invention to provide an improved method of monitoring the location of a surgical instrument within the body in conjunction with an ultrasound imaging system.

It is another object of the present invention to provide a significantly echogenically enhanced surgical instrument for use with an ultrasound imaging system.

Further objects and advantages will become apparent from the following description.

DESCRIPTION OF THE PREFERRED EMBODIMENT

Figure 1:
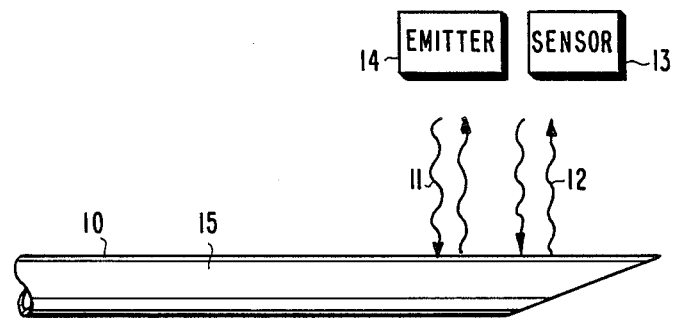
FIG. 1 is a side, elevational view of the end of a standard, virgin needle oriented axially 90° with respect to the direction of the incident ultrasound beam.

For the purposes of promoting an understanding of the principles of the invention, reference will now be made to the embodiment illustrated in the drawings and specific language will be used to describe the same. It will nevertheless be understood that no limitation of the scope of the invention is thereby intended, such alterations and further modifications in the illustrated device, and such further applications of the principles of the invention as illustrated therein being contemplated as would normally occur to one skilled in the art to which the invention relates.

The standard ultrasonic imaging system employed in the medical field is based upon the pulse-echo method wherein pulses of ultrasonic energy are periodically generated by a sizable piezoelectric transducer. Each short pulse of ultrasonic energy is focused to a narrow beam to pass into the patient's body wherein it eventually encounters the desired "target" surface. A portion of the ultrasonic energy is reflected back from the target surface to the ultrasound sensor for correlation and interpretation. The term echogenicity refers to the relative intrinsic or innate degree or extent that a surface reflects incident ultrasound wave energy directly back to the sensor, which is proximal to the source or emitter of the ultrasound system.

Figure 2:
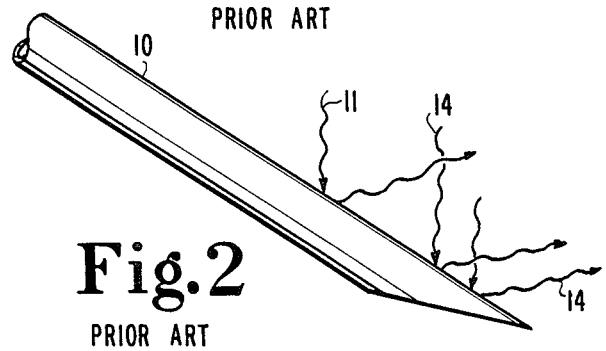
FIG. 2 is a side, elevational view of the needle of FIG. 1 axially oriented approximately 60° with respect to the incident ultrasound beam.

Shown in FIG. 1 is a standard, virgin needle 10 made of an appropriate material such as stainless steel. Needle 10 has a smooth outer surface 16 and is of the type commonly in use in the medical field. Needle 10 is most echogenic when it is at a right angle to incident ultrasound beames 11. The majority of the reflected beames 12 are picked up by a sensor (shown schematically at 13) which is located proximal to the source or emitter (shown schematically at 14) of incident beams 11. When needle 10 is oriented at an angle to the emitter and sensor, the "density" of direct echoes returned or reflected to the sensor decreases (FIG. 2). Althougth the density and elasticity of needle 10 do not change, the echogenicity of needle 10 is significantly decreased as the introductory or advancement angle of the needle 10 is varied away from 90° with respect to incident beams 11.

Figure 3:
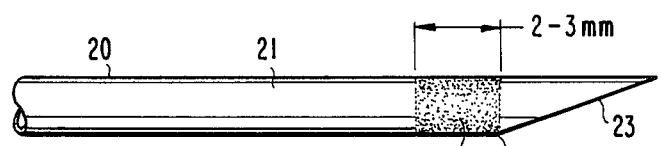
FIG. 3 is a side, elevational view of the end of a needle in accordance with the preferred embodiment of the present invention.
Figure 4:
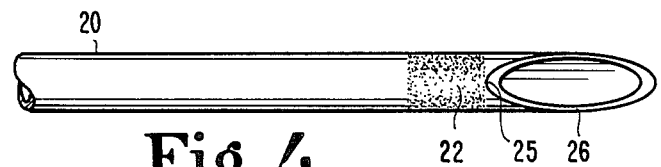
FIG. 4 is a bottom view of the needle of FIG. 3.

Shown in FIG. 3 is a needle 20 prepared in accordance with the preferred embodiment of the present invention. A virgin needle such as needle 10 shown in FIG. 1 is treated by particles-blasting a portion of the needle surface 21. The particle-blasted portion 22 is disposed upon outwardly facing surface 21 of needle 20 corresponding to that portion of the instrument which is desired to be monitored. For example, as the needle is inserted into the body to perform a tissue aspiration biopsy, it is desirable to know the absolute location of the tip or end 23 of needle 20. A single band apprroximately 2 to 3 millimeters in width is therefore created about the entire circumference of needle 20 just behind the trailing edge 25 of beveled opening 26 of needle 20 (FIGS. 3 and 4).

The particle-blasting of portion 22 includes the use of appropriate particles such as silicon dioxide, silicon carbide or other metal silicates. The particulate material of the preferred embodiment is silicon carbide. The particles used are in the range between sub-micron and 500 microns with the preferred particles size being between 1 and 100 microns. Using various particle sizes in the preferred range would add to the desired uniformly roughened topography. However, the most preferred particle size is approximately 50 microns. The treatment of needle 20 consists of uniformly particle-blasting the desired portion 22. The resulting surface portion 22 does not need to be deeply etched, blasted or mechanically eroded to significantly enhance the echogenicity of needle 20. The resulting pits or erosion need only be on the order of about 50 microns in depth. This, of course, will depend on the manner in which the particle-blasting is performed and upon the size particles used. The important factor is that portion 22 is uniformly roughened to produce an irregular surface topography.

Figure 5:
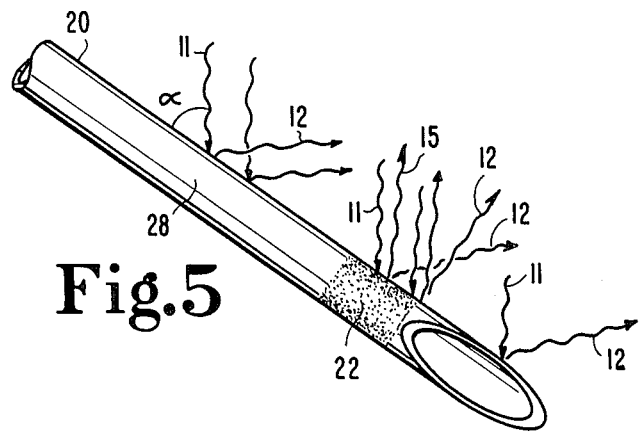
FIG. 5 is a bottom view of the needle of FIG. 4 which is oriented approximately 60° relative to the incident ultrasound beam.

As shown in FIG. 5, as the angle α between needle 20 and incident beams 11 is deviated farther from 90°, the incident ultrasound beams 11 upon untreated surface area 28 will result in an increasingly lower density of direct echoes returned to the sensor. The majority of reflected beams 12 will be scattered away from and not picked up by the sensor. Those incident beams 11 which strike the roughened surface 22 of needle 20, however, result in uniformly scattered echoes or reflected beams 12, which results in a significantly increased density of reflected beams 15 which reach the sensor. The result is a greatly enhanced echogenicity of the treated portion 22 of needle 20. A needle 20 treated in accordance with the present invention exhibits a relatively high density of direct echoes capable of collection by the sensor irrespective of the angle of the particle-blasted needle 20 relative to the incident ultrasound beams 11.

Figure 6:
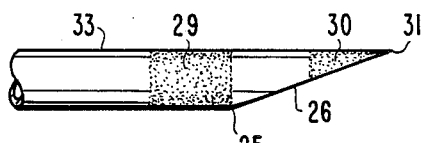
FIG. 6 is a side, elevational view of a portion of a needle in accordance with another embodiment of the present invention.
Figure 7:
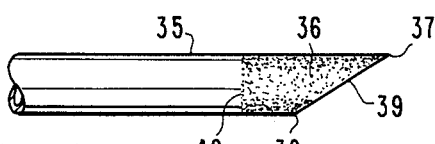
FIG. 7 is a side, elevational view of a portion of a needle in accordance with another embodiment of the present invention.

Alternative embodiments are contemplated wherein needle 33 contains multiple treated portions or one or more treated portions which have various geometric shapes. For example, in FIG. 6 needle 33 has a treated circumferential band 29 surrounding needle 33 just behind trailing edge 25 of beveled opening 26 as well as a treated beveled, circumferential portion 30 at the extreme leading edge of beveled opening 26. In FIG. 7, the entire end of needle 35 is treated producing a circumferential band 36 around needle 35 from its tip 37 to a ring 40 somewhere behind trailing edge 38 of bevelled portion 39. These, of coursr, would allow the operator to locate the extreme point or tip 31 or 37 of needle 33 or 35 during real-time imaging.

While the invention has been illustrated and described in detail in the drawings and foregoing description, the same is to be considered as illustrative and not restrictive in character, it being understood that only the preferred embodiment has been shown and described and that all changes and modifications that come within the spirit of the invention are described to be protected.

What is claimed is:

1. An echogenically enhanced surgical instrument for insertion into the body and used in conjunction with an ultrasound imaging system adapted to direct an incident beam of a given wavelength into the body, the instrument comprising:
   a smooth surface on that protion of the instrument which is to be inserted into the body,
   a roughened surface adjacent to said smooth surface and on that portion of the instrument which is to be inserted into the body, said roughened surface having a roughness between sub-micron and 500 microns, and
   wherein said smooth surface and said roughened surface define a recognizable and distinct border therebetween.

2. The echogenically enhanced surgical instrument of claim 1 wherein said roughened surface is randomly roughened by practicle-blasting.

3. The echogenically enhanced surgical instrument of claim 2 wherein the particle-blasting includes blasting with sand particles.

4. The echogenically enhanced surgical instrument of claim 2 wherein the particle-blasting includes blasting with particles having a size of between 1 and 100 microns.

5. The echogenically enhanced surgical instrument of claim 4 wherein the particle-blasting includes blasting with particles having a size of approximately 50 microns.

6. The echogenically enhanced surgical instrument of claim 1 wherein the surgical instrument is a needle having a leading edge and wherein said roughened surface is proximal to said leading edge.

7. The echogenically enhanced surgical instrument of claim 6 wherein said roughened surface defines a band surrounding said needle.

8. The echogenically enhanced surgical instrument of claim 1 wherein said roughened surface defines at least one specific geometric shape.

9. An echogenically enhanced surgical instrument for insertion into the body and used with an ultrasound imaging system adapted to direct an incident beam of a given wavelength into the body, the instrument comprising:

a surface on that portion of the instrument which is to be inserted into the body, the surface being randomly roughened by particle-blasting with particles having a size between sub-micron and 500 microns, the particle-blasting defining a distinctly recognizable geometric shape at a predetermined position along the instrument.

10. The echogenically enhanced surgical instrument of claim 9 wherein the particles are sand.

11. The echogenically enhanced surgical instrument of claim 9 wherein the particles have a size of between 1 and 100 microns.

12. The echogenically enhanced surgical instrument of claim 11 wherein the particles have a size of approximately 50 microns.

13. The echogenically enhanced surgical instrument of claim 9 wherein the particle-blasting is performed for a short period of time such that the average number of pits per unit area formed by the particle-blasting is very low.

14. The echogenically enhanced surgical instrument of claim 9 wherein the instrument is a needle having a leading edge and the roughened surface is proximal to the leading edge.

15. The echogenically enhanced surgical instrument of claim 11 wherein the roughened surface is a band surrounding the needle.

16. A method of producing a significantly echogenically enhanced surgical instrument for insertion into and guidance through the body and for use with an ultrasound imaging system, comprising the steps of:

providing a surgical instrument have a leading edge and a substantially smooth surface, both of which being on that position of the instrument which is to be inserted into the body; and particle-blasting a portion of said surface with particles having a size between sub-micron and 500 microns wherein said particle-blasted portion defines a recognizable and distinct border between the particle-blasted portion and the portion of said smooth surface which remains smooth.

17. The method of producing a significantly echogenically enhanced surgical instrument of claim 16 wherein said particle-blasting step includes blasting with sand particles.

18. The method of producing a significantly echogenically enhanced surgical instrument of claim 17 wherein the particle-blasting step further includes blasting with particles having a size of between 1 and 100 microns.

19. The method of producing a significantly echogenically enhanced surgical instrument of claim 18 wherein the particle-blasting step includes blasting with particles having a size of approximately 50 microns.

20. The method of producing a significantly echogenically enhanced surgical instrument of claim 16 wherein said particle-blasting step includes blasting said portion in a specific, predetermined shape.

21. The method of producing a significantly echogenically enhanced surgical instrument of claim 16 wherein said particle-blasting step includes blasting said portion proximal to the leading edge.

* * * * *

UNITED STATES PATENT AND TRADEMARK OFFICE
CERTIFICATE OF CORRECTION

PATENT NO. : 4,869,259

DATED : September 26, 1989

INVENTOR(S) : Dexter J. Elkins

It is certified that error appears in the above-identified patent and that said Letters Patent is hereby corrected as shown below:

In block 73 of the title page, the assignee should read --Vance Products Incorporated d/b/a Cook Urological Incorporated--.

In column 1, line 9, please change "systems" to --system--.

In column 1, line 31, please insert --the-- before "sensor".

In column 1, line 47, please change "granting" to --grating--.

In column 1, line 52, please change "$\lambda$" to --$\lambda_o$--.

In column 3, line 15, please change "beames" to --beams--.

In column 3, line 30, please change "particles-blasting" to --particle-blasting--.

In column 3, lines 37 and 38, please change "apprroximately" to --approximately--.

In column 3, line 47, please change "particles" to --particle--.

In column 4, line 23, please change "coursr" to --course--.

In column 4, line 44, please change "roughtened" to --roughened--.

UNITED STATES PATENT AND TRADEMARK OFFICE
CERTIFICATE OF CORRECTION

PATENT NO. : 4,869,259

DATED : September 26, 1989

INVENTOR(S) : Dexter J. Elkins

It is certified that error appears in the above-identified patent and that said Letters Patent is hereby corrected as shown below:

In column 4, line 53, please change "practicle-blasting"

--particle-blasting--.

Signed and Sealed this

Eighteenth Day of August, 1992

Attest:

DOUGLAS B. COMER

*Attesting Officer*   *Acting Commissioner of Patents and Trademarks*